(12) United States Patent
Yu et al.

(10) Patent No.: US 12,390,174 B2
(45) Date of Patent: Aug. 19, 2025

(54) DETECTOR MODULE, DETECTOR, AND MEDICAL DEVICE

(71) Applicant: Neusoft Medical Systems Co., Ltd., Liaoning (CN)

(72) Inventors: Jun Yu, Liaoning (CN); Tong Zhang, Liaoning (CN); Yiguang Tan, Liaoning (CN)

(73) Assignee: NEUSOFT MEDICAL SYSTEMS CO., LTD., Liaoning (CN)

( * ) Notice: Subject to any disclaimer, the term of this patent is extended or adjusted under 35 U.S.C. 154(b) by 273 days.

(21) Appl. No.: 18/299,030

(22) Filed: Apr. 11, 2023

(65) Prior Publication Data

US 2023/0240626 A1 Aug. 3, 2023

(30) Foreign Application Priority Data

Oct. 26, 2022 (CN) .......................... 202211317211.9

(51) Int. Cl.
*A61B 6/03* (2006.01)
*G01T 1/164* (2006.01)
(Continued)

(52) U.S. Cl.
CPC ............ *A61B 6/032* (2013.01); *G01T 1/1644* (2013.01); *G01T 1/2006* (2013.01); *G01T 1/243* (2013.01); *G01T 1/247* (2013.01)

(58) Field of Classification Search
CPC ...... A61B 6/032; G01T 1/1644; G01T 1/2006
See application file for complete search history.

(56) References Cited

U.S. PATENT DOCUMENTS

2012/0087465 A1* 4/2012 Ikhlef ...................... A61B 6/00
378/19
2016/0209521 A1* 7/2016 Jakubek ................ G01T 1/2928
(Continued)

FOREIGN PATENT DOCUMENTS

CN 102802531 A 11/2012
CN 108836376 A 11/2018
(Continued)

OTHER PUBLICATIONS

First Office Action dated Jul. 11, 2024 received in corresponding patent family application No. CN202211317211.9. English translation attached.

*Primary Examiner* — Hugh Maupin (57) ABSTRACT

Provide are a detector module, a detector, and a medical device. The detector module includes a plurality of detection sub-modules at least partially arranged in a stepped manner in a first direction. Each of the plurality of detection sub-modules includes a plurality of photoelectric conversion units arranged at intervals in a second direction intersecting with the first direction. One of two adjacent detection sub-modules is located at a higher step as a first detection sub-module, and the other one is located at a lower step and as a second detection sub-module. A first gap is formed between the plurality of photoelectric conversion units of the first detection sub-module. A second gap is formed between the plurality of photoelectric conversion units of the second detection sub-module. A width of the first gap in the second direction is smaller than a width of the second gap in the second direction.

20 Claims, 4 Drawing Sheets

(51) Int. Cl.
    *G01T 1/20*          (2006.01)
    *G01T 1/24*          (2006.01)

(56) References Cited

U.S. PATENT DOCUMENTS

| | | |
|---|---|---|
| 2017/0192107 A1* | 7/2017 | Li ........................ G01T 1/20187 |
| 2019/0239833 A1 | 8/2019 | Ikhelf |
| 2023/0063271 A1* | 3/2023 | Ikhlef ................... G01T 1/2985 |

FOREIGN PATENT DOCUMENTS

| | | |
|---|---|---|
| CN | 110664422 A | 1/2020 |
| CN | 111227859 A | 6/2020 |
| CN | 112022179 A | 12/2020 |
| JP | 2012040140 A | 3/2012 |

* cited by examiner

DETECTOR MODULE, DETECTOR, AND MEDICAL DEVICE

CROSS-REFERENCE TO RELATED APPLICATIONS

This application claims priority to Chinese Patent Application No. 202211317211.9 filed on Oct. 26, 2022, the entire disclosure of which is incorporated herein by reference.

FIELD

The present disclosure relates to the field of medical device technologies, and in particular, to a detector module, a detector, and a medical device.

BACKGROUND

With continuous development of medical levels, more and more medical devices are used to assist medical diagnosis or therapy. For example, a Computed Tomography (CT) device is used to detect human diseases. The CT device can detect an X-ray passing through a human body through a CT detector, and convert a received optical signal into an electrical signal.

A detector usually includes a plurality of detector modules in a direction Z. The plurality of detector modules is arranged in a stepped manner and has an arc-shaped outer contour in a direction X. In this case, widths of gaps between the detector modules in different steps in the direction X are different from each other. Further, as the number of steps of the detector increases, ununiformily irregular gaps with different widths would be formed, which is unfavorable for image reconstruction, thereby affecting a diagnosis result.

SUMMARY

The present disclosure aims to at least solve one of the technical problems in the related art.

To this end, a first aspect of the present disclosure provides a detector module.

A second aspect of the present disclosure provides a detector.

A third aspect of the present disclosure provides a medical device.

In view of this, according to the first aspect of embodiments of the present disclosure, a detector module is provided. The detector module includes a plurality of detection sub-modules at least partially arranged in a stepped manner in a first direction. Each of the plurality of detection sub-modules includes a plurality of photoelectric conversion units arranged at intervals in a second direction intersecting with the first direction. One of two adjacent detection sub-modules of the plurality of detection sub-modules is located at a higher step as a first detection sub-module, and the other one of the two adjacent detection sub-modules is located at a lower step and as a second detection sub-module. A first gap is formed between the plurality of photoelectric conversion units of the first detection sub-module. A second gap is formed between the plurality of photoelectric conversion units of the second detection sub-module. A width of the first gap in the second direction is smaller than a width of the second gap in the second direction.

In some embodiments of the present disclosure, each gap between the plurality of photoelectric conversion units of the first detection sub-module is the first gap; and/or each gap between the plurality of photoelectric conversion units of the second detection sub-module is the second gap.

In some embodiments of the present disclosure, a third gap is further formed between the plurality of photoelectric conversion units of the first detection sub-module, the third gap and the first gap being arranged in the second direction, and a width of the third gap in the second direction being different from the width of the first gap in the second direction; and/or a fourth gap is further present between the plurality of photoelectric conversion units of the second detection sub-module, the fourth gap and the second gap being arranged in the second direction, and a width of the fourth gap in the second direction being different from the width of the second gap in the second direction.

In some embodiments of the present disclosure, in the second direction, the width of the third gap is smaller than the width of the first gap, and the width of the fourth gap is smaller than the width of the second gap.

In some embodiments of the present disclosure, the width of the third gap in the second direction is equal to the width of the fourth gap in the second direction.

In some embodiments of the present disclosure, an odd number of gaps are formed between the plurality of photoelectric conversion units of the first detection sub-module, the first gap being alternately arranged with the third gap, and a head gap and a tail gap of the odd number of gaps are each the third gap. An odd number of gaps are present between the plurality of photoelectric conversion units of the second detection sub-module, the second gap being alternately arranged with the fourth gap, and a head gap and a tail gap of the odd number of gaps are each the fourth gap.

In some embodiments of the present disclosure, the plurality of photoelectric conversion units of the first detection sub-module has a same width in the second direction; and/or the plurality of photoelectric conversion units of the second detection sub-module has a same width in the second direction.

In some embodiments of the present disclosure, the plurality of photoelectric conversion units of the first detection sub-module has a same width as the plurality of photoelectric conversion units of the second detection sub-module in the second direction.

In some embodiments of the present disclosure, the detector module further includes a support, a substrate disposed on the support; and an analog-to-digital converter connected to the photoelectric conversion units. The photoelectric conversion units and the analog-to-digital converter are disposed on the substrate and arranged in the first direction. The substrate of the first detection sub-module is superposed on the analog-to-digital converter of the second detection sub-module.

According to a second aspect of embodiments of the present disclosure, a detector is provided. The detector includes a plurality of detector modules. Each of the plurality of detector modules is the detector module as described in any one of the embodiments of the present disclosure. The plurality of detector modules is arranged in the second direction, and detection sub-modules of the plurality of detector modules at a same step are adjacent to each other.

In some embodiments of the present disclosure, a fifth gap is formed between adjacent first detection sub-modules. A sixth gap is formed between adjacent second detection sub-modules. In the second direction, a width of the fifth gap is equal to the width of the first gap, and a width of the sixth gap is equal to the width of the second gap.

In some embodiments of the present disclosure, the detection sub-modules at the same step has surfaces tangent to circles with a same radius.

According to a third aspect of embodiments of the present disclosure, a medical device is provided. The medical device includes a housing defining a scanning chamber, and a detection assembly disposed in the housing. The detection assembly includes the detector as described in any one of the embodiments of the present disclosure. The first direction is an extending direction of the scanning chamber.

Compared with the related art, the present disclosure at least includes the following beneficial effects. The detector module according to the embodiments of the present disclosure includes the plurality of detection sub-modules. In operation, the radiation source can emit rays towards a scanned object. The radiation source may emit fan-shaped or conical ray beams, and each ray beam includes several rays. The radiation source can project the ray beams from its focus to the scanned object. The plurality of detection sub-modules of the detector module can detect a ray attenuated by the scanned object, convert an optical signal of the received ray into an electrical signal, and transmit the electrical signal to an upper computer for imaging. With the detector module according to the embodiments of the present disclosure, the plurality of detection sub-modules is at least partially arranged in the stepped manner in the first direction, and each of the plurality of detection sub-modules includes the plurality of photoelectric conversion units arranged at intervals in the second direction. With this arrangement, the detector module can include two or more layers of the detection sub-module arranged in the stepped manner. In this way, the gap between two adjacent detection sub-modules in the first direction can be reduced or eliminated as much as possible, to obtain more complete scanning data of a scanned part, thereby improving accuracy of a diagnosis result. Further, in a case where the detector includes the plurality of detector modules arranged in the second direction, a gap between the detector modules is difficult to be eliminated. In the detector module according to the embodiments of the present disclosure, in the case where the detector includes the plurality of detector modules, the first detection sub-module of the detector is arranged closer to the radiation source, and the second detection sub-module is arranged away from the radiation source relative to the first detection sub-module. Thus, the second detection sub-module away from the radiation source has a longer length (larger diameter) than the first detection sub-module closer to the radiation source. Thus, a larger gap is formed between two adjacent second detection sub-modules of the plurality of second detection sub-modules away from the radiation source. In addition, each of the plurality of detection sub-modules includes the plurality of photoelectric conversion units arranged at intervals in the second direction. One of two adjacent sub-modules of the plurality of detection sub-modules is located at the higher step as the first detection sub-module, and the other one of the two adjacent sub-modules is located at the lower step as the second detection sub-module. The first gap is formed between the plurality of photoelectric conversion units of the first detection sub-module. The second gap is formed between the plurality of photoelectric conversion units of the second detection sub-module. The width of the first gap in the second direction is smaller than the width of the second gap in the second direction. Therefore, the larger gap between two adjacent detection sub-modules in a same step can be shared into the detection sub-module. Thus, on one hand, the gaps between the detection sub-modules in the same step and the gaps in the detection sub-modules can be relatively uniformly arranged in the second direction, and on the other hand, a gap difference between detector sub-modules in adjacent steps can be reduced, which is beneficial to subsequent image reconstruction and improves diagnosis accuracy.

BRIEF DESCRIPTION OF THE DRAWINGS

Various other advantages and benefits will become apparent to those of ordinary skill in the art by reading the detailed description of preferred embodiments below. The accompanying drawings are merely for illustrating the preferred embodiments, rather than limiting the present disclosure. Moreover, throughout the accompanying drawings, same components/parts are denoted by same reference numerals. In the accompanying drawings.

Here, a correspondence between reference numerals and components in FIG. 1 to FIG. 10 is:

100 detector module;

110 detection sub-module, 120 support, 130 substrate, 140 analog-to-digital converter, 150 scintillator array, 160 protection plate;

111 first detection sub-module, 112 second detection sub-module, 113 photoelectric conversion unit, 114 first gap, 115 second gap, 116 third gap, 117 fourth gap, 118 photodiode array;

200 detector;

210 fifth gap, 220 sixth gap;

310 housing, 320 radiation source, 330 scanning opening, 340 bearing bed, 350 examiner.

DETAILED DESCRIPTION

The technical solutions of embodiments of the present disclosure will be described in detail below in combination with accompanying drawings and specific embodiments in order to better understand the above technical solutions. It should be understood that the embodiments of the present disclosure and specific features in the embodiments are detailed descriptions of the technical solutions of the embodiments of the present disclosure, rather than limiting the technical solutions of the present disclosure. The embodiments of the present disclosure or technical features in the embodiments can be combined to each other without contradiction.

A detector usually includes a plurality of detector modules in a direction Z. The plurality of detector modules is arranged in a stepped manner and has an arc-shaped outer contour in a direction X. In this case, widths of gaps between detector modules in different steps in the direction X are different from each other. Further, as the number of steps of the detector increases, nonuniform irregular gaps with different widths would be formed. The inventor of the present disclosure found that a large gap between adjacent detector modules and inner and outer gaps of the detector module are not uniform, both of which are unfavorable for subsequent image reconstruction.

As illustrated in FIG. 1 to FIG. 8, according to a first aspect of embodiments of the present disclosure, a detector module 100 is provided. The detector module 100 includes a plurality of detection sub-modules 110 at least partially arranged in a stepped manner in a first direction. Each of the plurality of detection sub-modules 110 includes a plurality of photoelectric conversion units 113 arranged at intervals in a second direction. One of two adjacent sub-modules of the plurality of detection sub-modules 110 is located at a higher step as a first detection sub-module 111, and the other one of the two adjacent sub-modules is located at a lower step as a second detection sub-module 112. A first gap 114 is formed between the plurality of photoelectric conversion units 113 of the first detection sub-module 111. A second gap 115 is formed between the plurality of photoelectric conversion units 113 of the second detection sub-module 112. A width of the first gap 114 in the second direction is smaller width than a width of the second gap 115 in the second direction. The first direction intersects with the second direction.

Figure 1:
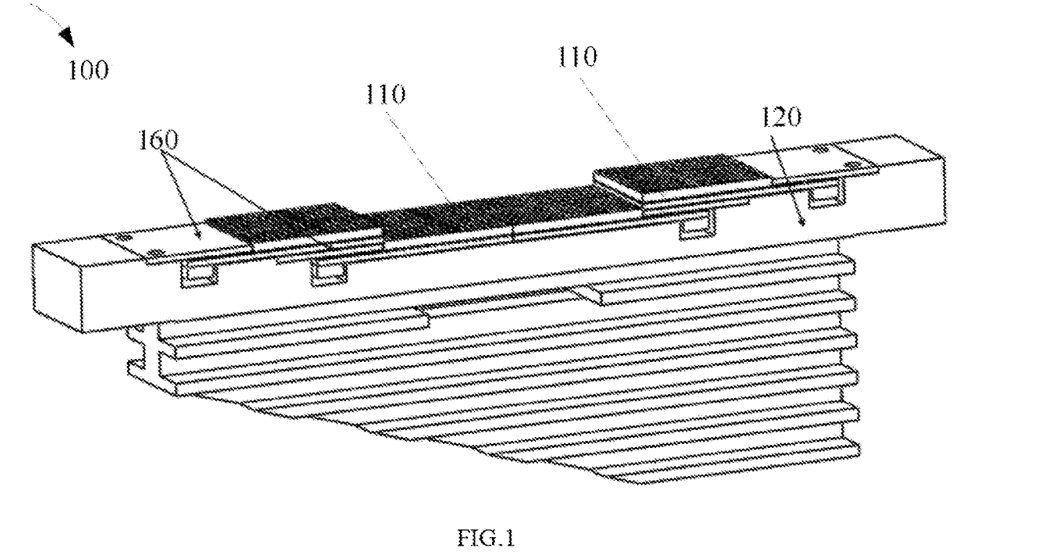
FIG. 1 is a schematic structural view of a detector module according to an embodiment of the present disclosure.
Figure 2:
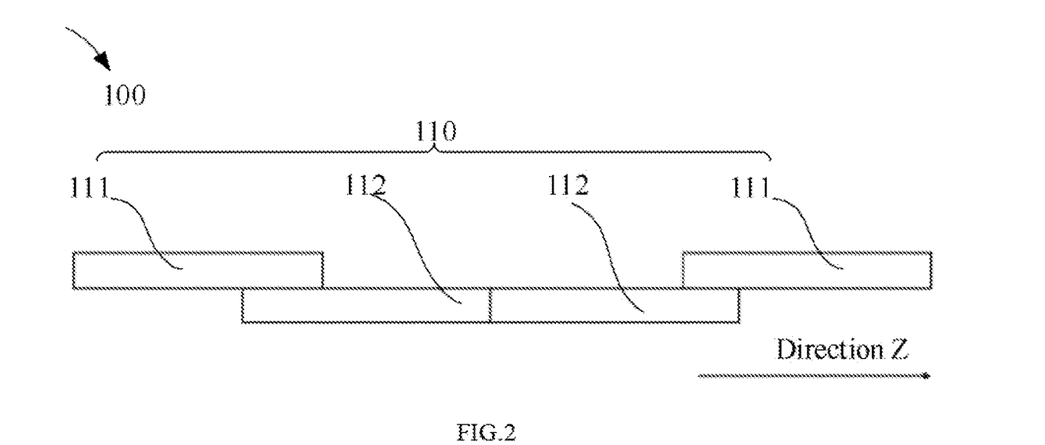
FIG. 2 is a schematic structural view of a detector module according to a first embodiment of the present disclosure at a viewing angle.
Figure 3:
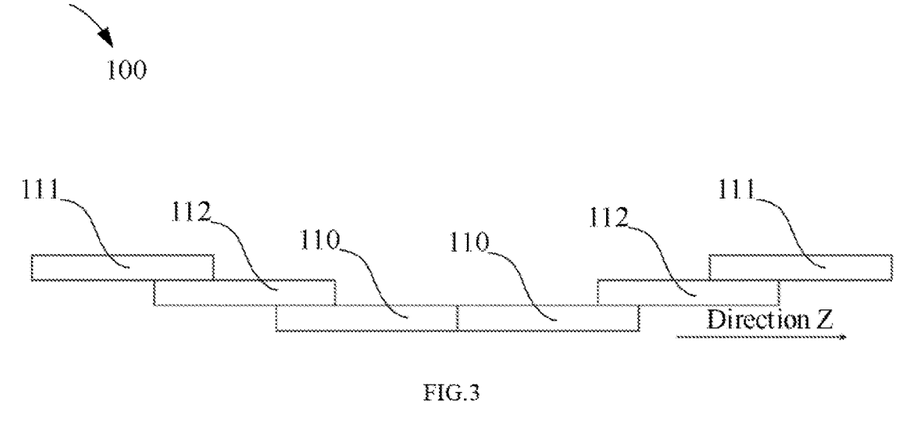
FIG. 3 is a schematic structural view of a detector module according to a second embodiment of the present disclosure at a viewing angle.
Figure 4:
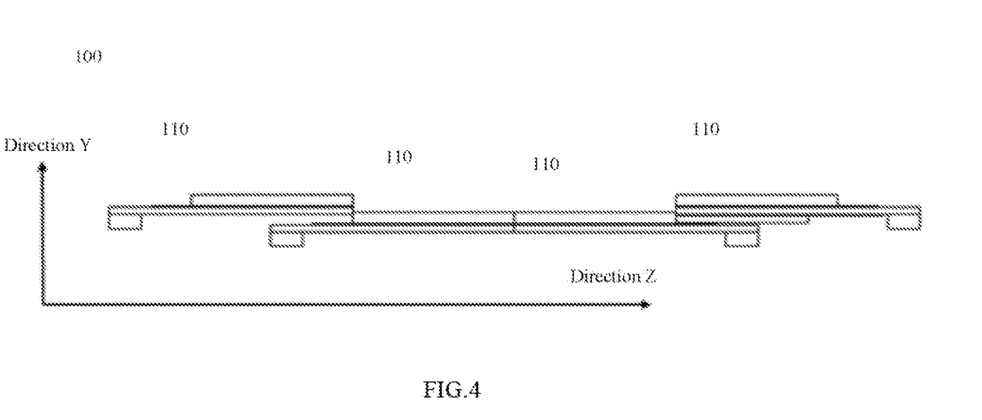
FIG. 4 is a schematic structural view of a detector module according to a third embodiment of the present disclosure at a viewing angle.

The detector module 100 according to the embodiments of the present disclosure includes the plurality of detection sub-modules 110. In operation, a radiation source 320 can emit rays towards a scanned object. The radiation source 320 may emit fan-shaped or conical ray beams, and each ray beam includes several rays. The radiation source 320 can project the ray beams from its focus to the scanned object. The plurality of detection sub-modules 110 of the detector module 100 is configured to detect a ray attenuated by the scanned object, convert an optical signal of the received ray into an electrical signal, and transmit the electrical signal to an upper computer for imaging.

With the detector module 100 according to the embodiments of the present disclosure, the plurality of detection sub-modules 110 is at least partially arranged in the stepped manner in the first direction, and each of the plurality of detection sub-modules 110 includes the plurality of photoelectric conversion units 113 arranged at intervals in the second direction. With this arrangement, the detector module 100 can include two or more layers of the detection sub-module 110 arranged in the stepped manner. In this way, the gap between two adjacent detection sub-modules 110 in the first direction can be reduced or eliminated as much as possible, to obtain more complete scanning data of a scanned part, thereby improving accuracy of a diagnosis result.

Figure 9:
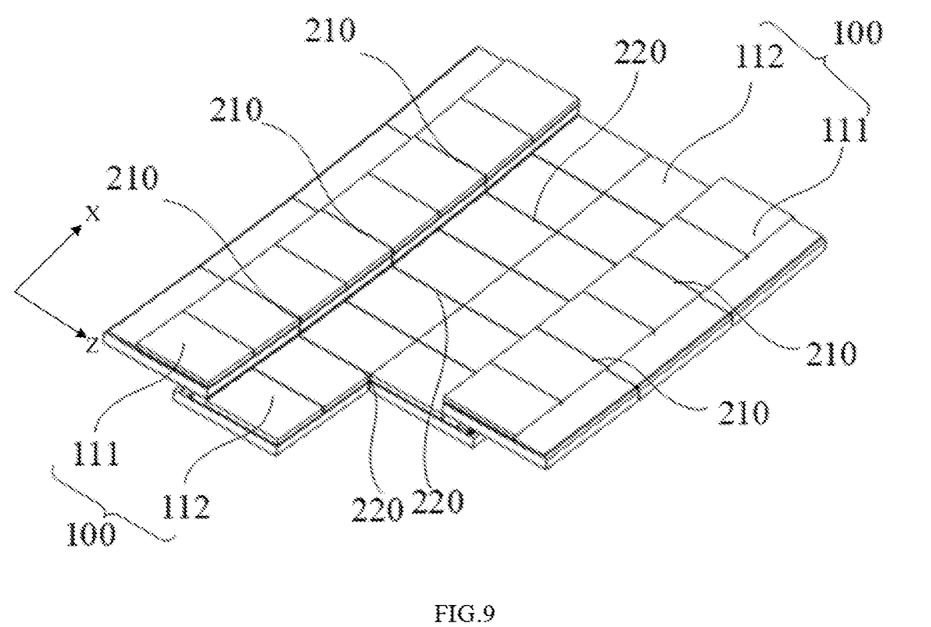
FIG. 9 is a schematic structural view of a detector according to an embodiment of the present disclosure.

Further, in a case where the detector 200 includes the plurality of detector modules 100 arranged in the second direction, a gap between the detector modules 100 is difficult to be eliminated. In the detector module 100 according to the embodiments of the present disclosure, in the case where the detector 200 includes the plurality of detector modules 100, the first detection sub-module 111 of the detector 200 is arranged closer to the radiation source 320, and the second detection sub-module 112 is arranged away from the radiation source 320 relative to the first detection sub-module 111. Thus, the second detection sub-module 112 away from the radiation source 320 has a longer length than the first detection sub-module 111 closer to the radiation source 320. That is, a radius of a step where the first detection sub-module is located is smaller than a radius of a step where the second detector sub-module is located, so that a larger gap is formed between two adjacent second detection sub-modules 112 of the plurality of second detection sub-modules 112 away from the radiation source 320. In addition, each of the plurality of detection sub-modules 110 includes the plurality of photoelectric conversion units 113 arranged at intervals in the second direction. One of two adjacent sub-modules of the plurality of detection sub-modules 110 is located at the higher step as the first detection sub-module 111, and the other one of the two adjacent sub-modules is located at the lower step as the second detection sub-module 112. The first gap 114 is formed between the plurality of photoelectric conversion units 113 of the first detection sub-module 111. The second gap 115 is formed between the plurality of photoelectric conversion units 113 of the second detection sub-module 112. The width of the first gap 114 in the second direction is smaller than the width of the second gap 115 in the second direction. Therefore, the larger gap between two adjacent detection sub-modules in a same step can be shared into the detection sub-module 110. Thus, on one hand, the gaps between the detection sub-modules 110 in the same step and the gaps in the detection sub-modules can be relatively uniformly arranged in the second direction, and on the other hand, a gap difference between detector sub-modules in adjacent steps can be reduced, which is beneficial to subsequent image reconstruction and improves diagnosis accuracy.

With the detector module 100 according to the embodiments of the present disclosure, the first gap 114 is formed between the plurality of photoelectric conversion units 113 of the first detection sub-module 111. The second gap 115 is formed between the plurality of photoelectric conversion units 113 of the second detection sub-module 112. It should be understood that the first detection sub-module 111 may include at least two photoelectric conversion units 113, and at least one gap may be formed between the plurality of photoelectric conversion units 113. With the detector module 100 according to the embodiments of the present disclosure, the plurality of gaps in the first detection sub-module 111 includes the first gap. It should be noted that the first gap 114 may be one, two, or more gaps. Similarly, the second detection sub-module 112 may include at least two photoelectric conversion units 113, and at least one gap may be formed between the at least two photoelectric conversion units 113. In the detector module 100 according to the embodiments of the present disclosure, the plurality of gaps in the second detection sub-module 112 may include the second gap. It should be noted that the second gap 114 may be one, two, or more gaps.

It should be understood that, as illustrated in FIG. 2 to FIG. 4 and FIG. 7, the first direction is a direction Z, the second direction is a direction X. The direction Z may refer to a width direction of the detector, a feeding direction of a scanning bed, or an extending direction of a scanning chamber. The first direction is perpendicular to the second direction. A direction Y can be defined as a third direction, and may refer to a height direction of the detector module. The first direction, the second direction, and the third direction are perpendicular to each other.

In a feasible implementation, each gap between the plurality of photoelectric conversion units 113 of the first detection sub-module 111 is the first gap 114, and/or each gap between the plurality of photoelectric conversion units 113 of the second detection sub-module 112 is the second gap 115.

In this technical solution, an arrangement of the gaps in the first detection sub-module III is further provided. The plurality of photoelectric conversion units 113 is included in the first detection sub-module 111. Therefore, a plurality of gaps can be formed between the plurality of photoelectric conversion units 113, and each of the plurality of gaps is the first gap 114. That is, the gaps between the first detection sub-modules are equally distributed into the first detection sub-module. With this arrangement, production and processing of the first detection module are facilitated, which can reduce processing difficulty.

In this technical solution, an arrangement of the gaps in the second detection sub-module 112 is further provided. The plurality of photoelectric conversion units 113 is included in the second detection sub-module 112. Therefore, a plurality of gaps may be formed between the plurality of photoelectric conversion units 113, and each of the plurality of gaps is the second gap 115. That is, the gaps between the second detection sub-modules 112 are equally distributing into the first detection sub-module. With this arrangement, production and processing of the second detection module are facilitated, which can reduce the processing difficulty.

Figure 5:
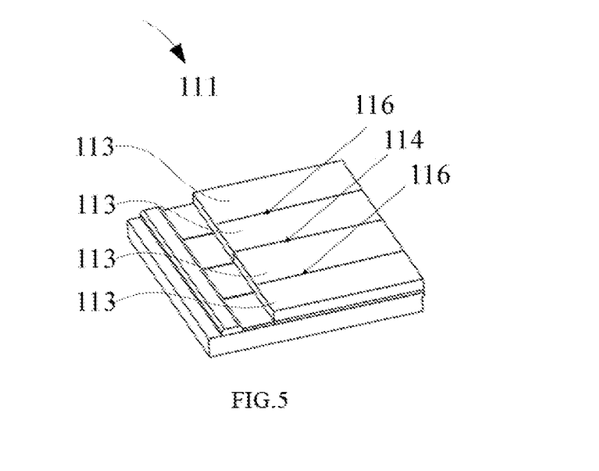
FIG. 5 is a schematic structural view of a first detection sub-module of a detector module according to an embodiment of the present disclosure.
Figure 6:
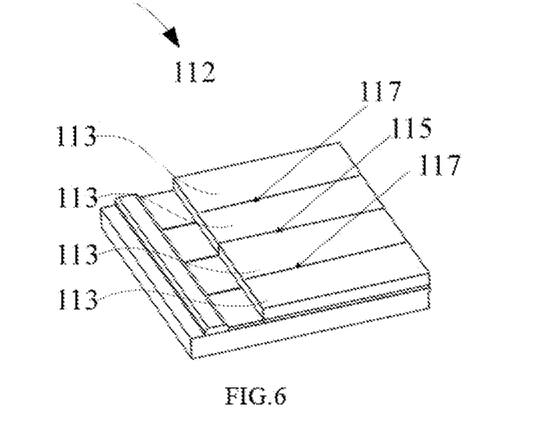
FIG. 6 is a schematic structural view of a second detection sub-module of a detector module according to an embodiment of the present disclosure.

As illustrated in FIG. 5 and FIG. 6, in a feasible implementation, a third gap 116 is further formed between the plurality of photoelectric conversion units 113 of the first detection sub-module 111, the third gap 116 and the first gap 114 are arranged in the second direction, and a width of the third gap 116 in the second direction is different from the width of the first gap 114 in the second direction; and/or a fourth gap 117 is further formed between the plurality of photoelectric conversion units 113 of the second detection sub-module 112, the fourth gap 117 and the second gap 115 are arranged in the second direction, and a width of the fourth gap 117 in the second direction is different from the width of the second gap 115 in the second direction.

In this technical solution, another arrangement of the gaps in the first detection sub-module 111 is further provided. The plurality of photoelectric conversion units 113 is included in the first detection sub-module 111. Therefore, a plurality of gaps can be formed between the plurality of photoelectric conversion units 113. Further, some of the plurality of gaps are the first gap 114, and some of the plurality of gaps are the third gap 116. Moreover, the third gap 116 has the different width from the first gap 114. In this way, in a processing process of the detector module 100, the gap between the two adjacent detection sub-modules 110 at the same step and the gaps in the detection sub-module can be relatively uniformly arranged in the second direction by only changing an arrangement position of the photoelectric conversion unit 113 in the middle of the detection sub-module 110. Therefore, the gap difference between the detection sub-modules in different steps can be reduced even to zero.

In this technical solution, another arrangement of the gaps in the second detection sub-module 112 is further provided. The plurality of photoelectric conversion units 113 is included in the second detection sub-module 112. Therefore, a plurality of gaps can be formed between the plurality of photoelectric conversion units 113. Further, some of the plurality of gaps are the second gap 115, and some of the plurality of gaps are the fourth gap 117. Moreover, the width of the fourth gap 117 is different from the width of the second gap 115. In this way, in the processing process of the detector module 100, the gap between the two adjacent detection sub-modules 110 at the same step and the gaps in the detection sub-module can be relatively uniformly arranged in the second direction by only changing the arrangement position of the photoelectric conversion unit 113 in the middle of the detection sub-module 110. Therefore, the gap difference between the detection sub-modules in different steps can be reduced even to zero.

As illustrated in FIG. 5 and FIG. 6, in a feasible implementation, in the second direction, the width of the third gap 116 is smaller than the width of the first gap 114, and the width of the fourth gap 117 is smaller than the width of the second gap 115.

In this technical solution, a width relationship between the third gap 116 and the first gap 114 and a width relationship between the fourth gap 117 and the second gap 115 are further provided. The width of the third gap 116 is smaller than the width of the first gap 114. The width of the fourth gap 117 is smaller than the width of the second gap 115. Each of the width of the third gap 116 and the width of the fourth gap 117 in the second direction can be understood as a basic width. Each of the width of the first gap 114 and the width of the second gap 115 in the second direction can be understood as an adjusted width for adjusting the gap between the detection sub-modules. With this arrangement, the gap between different detection sub-modules 110 of the detector 200 at the same step in the second direction can be adjusted by the arrangement of some of the first gaps 114 and the arrangement of some of the second gaps 115, which is beneficial to the image reconstruction and can improve the diagnosis accuracy.

As illustrated in FIG. 5 and FIG. 6, in a feasible implementation, the width of the third gap 116 is equal to the width of the fourth gap 117 in the second direction.

In this technical solution, a width relationship between the third gap 116 and the fourth gap 117 is further provided. The width of the third gap 116 is equal to the width of the fourth gap 117. Based on this, a difference between the first detection sub-module 111 and the second detection sub-module 112 becomes smaller, so that the difference between the first detection sub-module 111 and the second detection sub-module 112 is only in the difference between the first gap 114 and the second gap 115. With this arrangement, the detection sub-modules 110 at different steps can be conveniently produced and processed, which can improve processing and assembly efficiency of the detector module.

As illustrated in FIG. 5 and FIG. 6, in a feasible implementation, an odd number of gaps are formed between the plurality of photoelectric conversion units 113 of the first detection sub-module 11. Further, the first gap 114 is alternately arranged with the third gap 116, and a head gap and a tail gap of the odd number of gaps are each the third gap 116. In addition, an odd number of gaps are formed between the plurality of photoelectric conversion units 113 of the second detection sub-module 112. Further, the second gap 115 is alternately arranged with the fourth gap 117, and a head gap and a tail gap of the odd number of gaps are each the fourth gaps 117.

In this technical solution, an arrangement of the first gaps 114 and the third gaps 116 is further provided in a case where both the first gap 14 and the third gap 116 are formed between the plurality of photoelectric conversion units 113 of the first detection sub-module 111. The first gap 114 is alternately arranged with the third gap 116, and a head gap and a tail gap among the first gap 14 and the third gap 116 are each the third gaps 116. In the detector 200, the gap between the first detection sub-modules 111 and the first gap 114, or adjacent first gaps 114 are spaced apart from each other by the third gap 116. With this arrangement, the gaps between the detection sub-modules at the same step and the gaps in the detection sub-module are relatively uniform and regularly arranged, which is beneficial to the image reconstruction.

In this technical solution, an arrangement of the second gaps 115 and the fourth gaps 117 is further provided in a case of both the second gap 115 and the fourth gap 117 are formed between the plurality of photoelectric conversion units 113 of the second detection sub-module 112. The second gap 115 is alternately arranged with the fourth gap 117, and a head gap and a tail gap among the second gap 115 and the fourth gap 117 are each the third gap the fourth gaps 117 are arranged at head and tail positions. In the detector 200, the gap between the second detection sub-module 112 and the second gap 115, or adjacent second gaps 115 are spaced apart from each other by the fourth gap 117. With this arrangement, the gaps between the detection sub-modules at the same step and the gaps in the detection sub-module are relatively uniform and regularly arranged, which is beneficial to the image reconstruction.

As illustrated in FIG. 5 and FIG. 6, in a feasible implementation, the plurality of photoelectric conversion units 113 of the first detection sub-module 111 has a same width in the second direction; and/or the plurality of photoelectric conversion units 113 of the second detection sub-module 112 has a same width in the second direction.

In this technical solution, a relationship between the plurality of photoelectric conversion units 113 in each first detection sub-module 111 is further provided, in which the plurality of photoelectric conversion units 113 of the first detection sub-module 111 has the same width. In this way, the plurality of photoelectric conversion units 113 has a same structure, thereby facilitating production and assembly of the first detection sub-module 111.

In this technical solution, a relationship between the plurality of photoelectric conversion units 113 in each second detection sub-module 112 is further provided, in which the plurality of photoelectric conversion units 113 of the second detection sub-module 112 has the same width. In this way, the plurality of photoelectric conversion units 113 has a same structure, thereby facilitating production and assembly of the second detection sub-module 112.

In a feasible implementation, the width of each of the plurality of photoelectric conversion units 113 of the first detection sub-module 111 is the same as the width of each of the plurality of photoelectric conversion units 113 of the second detection sub-module 112 in the second direction.

In this technical solution, parameter information of the photoelectric conversion unit 113 between the first detection sub-module 111 and the second detection sub-module 112 is further provided. The width of each of the plurality of photoelectric conversion units 113 of the first detection sub-module 111 is the same as the width of each of the plurality of photoelectric conversion units 113 of the second detection sub-module 112. With this arrangement, a difference between the detection sub-modules 110 in different steps can be further reduced, so that the detection sub-modules 110 in the different steps can use the same photoelectric conversion unit 113. Thus, it is possible to reduce production cost and improve detection precision.

Figure 7:
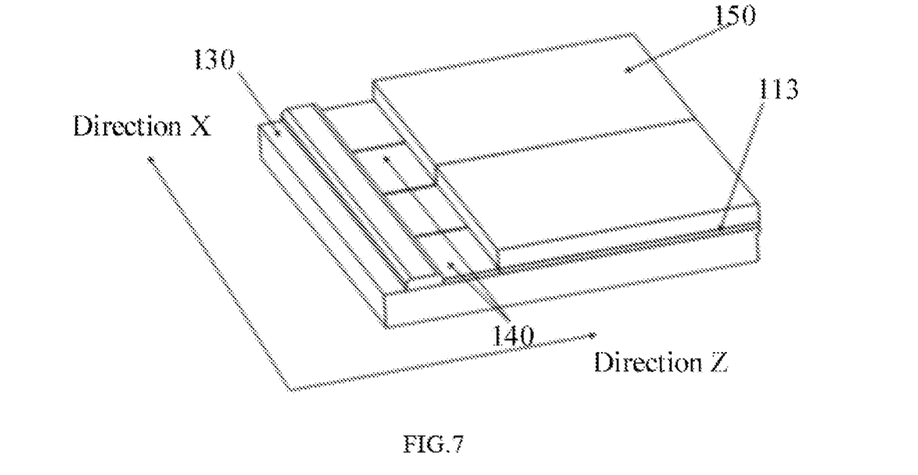
FIG. 7 is a schematic structural view of a detection sub-module of a detector module according to an embodiment of the present disclosure.
Figure 8:
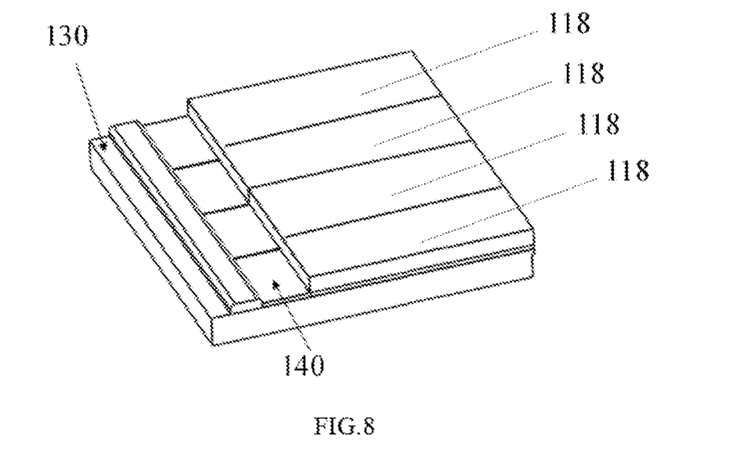
FIG. 8 is a schematic structural view of a photoelectric conversion unit of a detection sub-module of a detector module according to an embodiment of the present disclosure.

As illustrated in FIG. 1, FIG. 7, and FIG. 8, in a feasible implementation, the detector module 100 further includes a support 120, a substrate 130, and an analog-to-digital converter 140. The analog-to-digital converter 140 is connected to the photoelectric conversion unit 113. The photoelectric conversion unit 113 and the analog-to-digital converter 140 are disposed on the substrate 130 and arranged in the first direction. The substrate 130 is disposed on the support 120. The substrate 130 of the first detection sub-module 111 is superposed on the analog-to-digital converter 140 of the second detection sub-module 112.

In this technical solution, a structural composition of the detector module 100 is further provided. The detection module may include the support 120, the substrate 130, and the analog-to-digital converter 140. The support 120 can support and fix the plurality of detection sub-modules 110. The substrate 130 can provide mounting positions for the photoelectric conversion unit 113 and the analog-to-digital converter 140. The analog-to-digital converter 140 is configured to transmit a signal.

In some examples, the photoelectric conversion unit 113 may include a photodiode array 118, and the detector module 100 may further include a scintillator array 150 disposed on the photodiode array 118. The scintillator array 150 is configured to receive the rays attenuated by the scanned object and convert the rays into visible light. The photodiode array 118 is configured to obtain an electrical signal based on the visible light.

It should be understood that the substrate 130 serves as a carrier for carrying the scintillator array 150 and the photodiode array 118 and transmitting an electrical signal generated by the photodiode array 118 to the analog-to-digital converter 140 by using a CMOS integrated circuit technology. A traditional circuit technology for connecting lines and circuit boards is replaced with the CMOS integrated circuit technology, which can shorten a signal transmission distance, reduces interference factors during signal transmission, and facilitate image quality improvement. Meanwhile, such analog-to-digital converter 140 can be biased at low cost.

As illustrated in FIG. 1, in some examples, the detector module 100 further includes a protection plate 160 disposed on a side of each of the plurality of detection sub-modules 110 away from the support 120.

In this technical solution, the protection plate 160 is configured to protect the analog-to-digital converter 140 of the detection sub-module 110 from the damage on the analog-to-digital converter 140 due to the rays.

In some examples, the protection plate 160 may be a tungsten sheet. It should be understood that other metal sheets having a protective function are suitable in the present disclosure.

As illustrated in FIG. 9, according to a second aspect of the embodiments of the present disclosure, a detector 200 is provided. The detector includes a plurality of detector modules according to any one of the above technical solutions. The plurality of detector modules 100 is arranged in the second direction. Detection sub-modules 110 of the plurality of detector modules 100 at the same step are adjacent to each other.

The detector 200 according to the embodiments of the present disclosure includes the plurality of detector modules 100 according to any one of the above technical solutions. Therefore, the detector 200 has all beneficial effects of the detector module 100 as described in the above technical solutions.

The detector 200 according to the embodiments of the present disclosure includes the plurality of detector modules 100 arranged in the second direction. In addition, the first detection sub-module 111 of each of the plurality of detector modules 100 at a higher step is the first detection sub-module 111, and the detection sub-module 111 of each of the plurality of detector modules 100 at a lower step is the second detection sub-module 112. The first gaps 114 are formed between the plurality of photoelectric conversion units 113 of the first detection sub-module 111. The second gaps 115 are formed between the plurality of photoelectric conversion units 113 of the second detection sub-module 112. The width of each first gap 114 is smaller than the width of each second gap 115 in the second direction. Thus, the larger gap between the two adjacent detection sub-modules can be shared into the detection sub-module 110. Therefore, on one hand, the gaps between the detection sub-modules 110 in the same step and the gaps in the detection sub-modules can be relatively uniformly arranged in the second direction, and on the other hand, a gap difference between detector sub-modules in adjacent steps can be reduced, which is beneficial to subsequent image reconstruction and improves the diagnosis accuracy.

In a feasible implementation, a fifth gap 210 is formed between adjacent first detection sub-modules 111, and a sixth gap 220 is formed between adjacent second detection sub-modules 112. In the second direction, the fifth gap 210 has an equal width to the first gap 114, and the sixth gap 220 has an equal width to the second gap 115.

In this technical solution, value ranges of the fifth gap 210 and the sixth gap 220 are further provided. The fifth gap 210 has the equal width to the first gap 114, and the sixth gap 220 has the equal width to the second gap 115. With this arrangement, it is possible for the gap between two adjacent detection sub-modules in the detector 200 at the same step in the second direction to be same as at least some of the gaps in the detection sub-module. Further, it is also possible for the sixth gap 220 in adjacent steps to approach the fifth gap 210. With this arrangement, it is beneficial to relative uniform arrangement of the gaps in the detector 200, and the gaps include the gap between the detection sub-modules and the gap in the detection sub-module. Therefore, it is possible to facilitate the image reconstruction and improve the diagnosis accuracy.

In a feasible implementation, each of the detection sub-modules 110 at the same step has a surface tangent to a circle with a same radius.

In this technical solution, an arrangement of the detection sub-modules 110 at the same step is further provided, in which each of the detection sub-modules 110 at the same step has the surface tangent to the circle with the same radius. Therefore, the fan-shaped or conical ray beams emitted from the radiation source 320 can be better adapted, which enables the rays to substantially vertically be incident onto a surface of the photoelectric conversion unit 113. Thus, the detection precision is improved.

Figure 10:
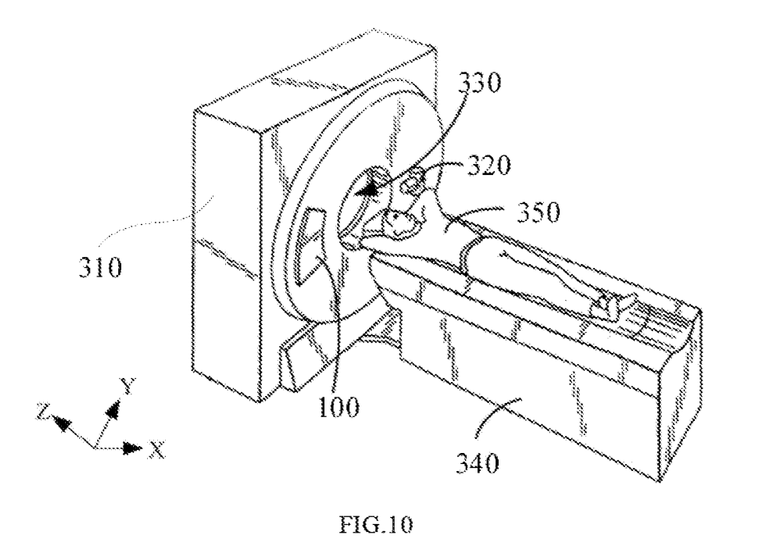
FIG. 10 is a schematic structural view of a medical device according to an embodiment of the present disclosure.

According to a third aspect of the embodiments of the present disclosure, a medical device is provided. The medical device includes a housing 310 and a detection assembly disposed in the housing 310. A scanning chamber is formed within the housing 310. The detection assembly includes the detector 200 according to any one of the above technical solutions. The first direction is an extending direction of the scanning chamber.

It should be understood that the medical device according to the embodiments of the present disclosure includes the detector 200 according to any one of the above technical solutions. Therefore, the medical device has all the beneficial effects of the detector 200 as described in the above technical solutions, and the description thereof in detail will be omitted herein.

As illustrated in FIG. 10, in some examples, a scanning opening 330 may be formed on the medical device, and an examiner 350 can lie on a bearing bed 340 to be moved into the scanning opening 330 by moving the bearing bed 340. Further, the radiation source 320 can emit the rays to the scanned object. The radiation source 320 may emit the fan-shaped or conical ray beams, and each ray beam includes several rays. The radiation source 320 can projects the ray beams from its focus to the scanned object. The plurality of detector modules 110 of the detector 200 is configured to detect rays attenuated by the scanned object, convert the optical signal of the received ray into the electrical signal, and retransmit the electrical signal to the upper computer for imaging.

In the present disclosure, the terms "first", "second", "third", etc., are merely for description, and cannot be understood as indicating or implying relative importance. It should be understood that "a plurality of" referred to herein means two or more, unless specified otherwise. Terms such as "installation", "connection", "connected to", "fixed" and the like should be understood in a broad sense. For example, "connection" may be a fixed connection or a detachable connection or an integral connection; "connected to" may be directly or indirectly connected through an intermediate. For those of ordinary skill in the art, the specific meaning of the above-mentioned terms in the present disclosure can be understood according to specific circumstances.

In the description of the present disclosure, it should be understood that, orientations or position relationships indicted by terms such as "upper", "lower", "left", "right" "front", "back", and the like, are based on orientations or position relationships shown in the accompanying drawings, and is merely for the convenience of describing the present disclosure and simplifying the description, rather than indicating or implying that the associated device or element must have a specific orientation, or be constructed and operated in a specific orientation, and therefore cannot be understood as a limitation on the present disclosure.

In the description of this specification, descriptions with reference to the terms "an embodiment", "some embodiments", "specific embodiments", or the like, mean that specific features, structure, materials or characteristics described in conjunction with the embodiment or example are included in at least one embodiment or example of the present disclosure. In this specification, the schematic representations of the above terms do not necessarily refer to the same embodiment or example. Moreover, the described specific features, structures, materials or characteristics may be combined in any one or more embodiments or examples in a suitable manner.

While preferred embodiments of the present disclosure have been described above, the present disclosure is not limited thereto. For those skilled in the art, various changes and modifications can be made to the present disclosure. Any modification, equivalent replacement, improvement, etc., made within the spirit and principle of the present disclosure shall fall within the scope of the present disclosure.

What is claimed is:

1. A detector module, comprising a plurality of detection sub-modules at least partially arranged in a stepped manner in a first direction, wherein:

each of the plurality of detection sub-modules comprises a plurality of photoelectric conversion units arranged at intervals in a second direction intersecting with the first direction and one substrate, the plurality of photoelectric conversion units being disposed on the substrate to share the substrate;
one of two adjacent detection sub-modules of the plurality of detection sub-modules is located at a higher step as a first detection sub-module, and the other one of the two adjacent detection sub-modules is located at a lower step and as a second detection sub-module;
a first gap is formed between the plurality of photoelectric conversion units of the first detection sub-module;
a second gap is formed between the plurality of photoelectric conversion units of the second detection sub-module; and
a width of the first gap in the second direction is smaller than a width of the second gap in the second direction.

2. The detector module according to claim 1, wherein:
each gap between the plurality of photoelectric conversion units of the first detection sub-module is the first gap; and/or
each gap between the plurality of photoelectric conversion units of the second detection sub-module is the second gap.

3. The detector module according to claim 1, wherein:
a third gap is further formed between the plurality of photoelectric conversion units of the first detection sub-module, the third gap and the first gap being arranged in the second direction, and a width of the third gap in the second direction being different from the width of the first gap in the second direction; and/or
a fourth gap is further present between the plurality of photoelectric conversion units of the second detection sub-module, the fourth gap and the second gap being arranged in the second direction, and a width of the fourth gap in the second direction being different from the width of the second gap in the second direction.

4. The detector module according to claim 3, wherein in the second direction, the width of the third gap is smaller than the width of the first gap, and the width of the fourth gap is smaller than the width of the second gap.

5. The detector module according to claim 4, wherein the width of the third gap in the second direction is equal to the width of the fourth gap in the second direction.

6. The detector module according to claim 4, wherein:
an odd number of gaps are formed between the plurality of photoelectric conversion units of the first detection sub-module, the first gap being alternately arranged with the third gap, and a head gap and a tail gap of the odd number of gaps are each the third gap; and
an odd number of gaps are present between the plurality of photoelectric conversion units of the second detection sub-module, the second gap being alternately arranged with the fourth gap, and a head gap and a tail gap of the odd number of gaps are each the fourth gap.

7. The detector module according to claim 1, wherein:
the plurality of photoelectric conversion units of the first detection sub-module has a same width in the second direction; and/or
the plurality of photoelectric conversion units of the second detection sub-module has a same width in the second direction.

8. The detector module according to claim 7, wherein the plurality of photoelectric conversion units of the first detection sub-module has a same width as the plurality of photoelectric conversion units of the second detection sub-module in the second direction.

9. The detector module according to claim 1, further comprising:
a support on which the substrates of the plurality of detection sub-modules are disposed;
wherein each of the plurality of detection sub-modules further comprises an analog-to-digital converter connected to the plurality of photoelectric conversion units of the detection sub-module, the plurality of photoelectric conversion units and the analog-to-digital converter of the detection sub-module being disposed on the substrate of the detection sub-module and arranged in the first direction,
wherein the substrate of the first detection sub-module being superposed on the analog-to-digital converter of the second detection sub-module.

10. A detector, comprising a plurality of detector modules, each of the plurality of detector modules comprising a plurality of detection sub-modules at least partially arranged in a stepped manner in a first direction, wherein:
each of the plurality of detection sub-modules comprises a plurality of photoelectric conversion units arranged at intervals in a second direction intersecting with the first direction and one substrate, the plurality of photoelectric conversion units being disposed on the substrate to share the substrate;
one of two adjacent detection sub-modules is located at a higher step as a first detection sub-module, and the other one of the two adjacent detection sub-modules is located at a lower step and as a second detection sub-module;
a first gap is formed between the plurality of photoelectric conversion units of the first detection sub-module;
a second gap is formed between the plurality of photoelectric conversion units of the second detection sub-module;
a width of the first gap in the second direction is smaller than a width of the second gap in the second direction; and
the plurality of detector modules is arranged in the second direction, and detection sub-modules of the plurality of detector modules at a same step are adjacent to each other.

11. The detector according to claim 10, wherein:
a fifth gap is formed between adjacent first detection sub-modules;
a sixth gap is formed between adjacent second detection sub-modules; and
in the second direction, a width of the fifth gap is equal to the width of the first gap, and a width of the sixth gap is equal to the width of the second gap.

12. The detector according to claim 10, wherein the detection sub-modules at the same step have surfaces tangent to circles with a same radius.

13. The detector according to claim 10, wherein:
each gap between the plurality of photoelectric conversion units of the first detection sub-module is the first gap; and/or
each gap between the plurality of photoelectric conversion units of the second detection sub-module is the second gap.

14. The detector according to claim 10, wherein:
a third gap is further formed between the plurality of photoelectric conversion units of the first detection sub-module, the third gap and the first gap being arranged in the second direction, and a width of the third gap in the second direction being different from the width of the first gap in the second direction; and/or a fourth gap is further present between the plurality of photoelectric conversion units of the second detection sub-module, the fourth gap and the second gap being arranged in the second direction, and a width of the fourth gap in the second direction being different from the width of the second gap in the second direction.

15. The detector according to claim 14, wherein in the second direction, the width of the third gap is smaller than the width of the first gap, and the width of the fourth gap is smaller than the width of the second gap.

16. The detector according to claim 15, wherein the width of the third gap in the second direction is equal to the width of the fourth gap in the second direction.

17. The detector according to claim 15, wherein:

an odd number of gaps are formed between the plurality of photoelectric conversion units of the first detection sub-module, the first gap being alternately arranged with the third gap, and a head gap and a tail gap of the odd number of gaps are each the third gap; and an odd number of gaps are present between the plurality of photoelectric conversion units of the second detection sub-module, the second gap being alternately arranged with the fourth gap, and a head gap and a tail gap of the odd number of gaps are each the fourth gap.

18. The detector according to claim 10, wherein:

the plurality of photoelectric conversion units of the first detection sub-module has a same width in the second direction; and/or the plurality of photoelectric conversion units of the second detection sub-module has a same width in the second direction.

19. The detector according to claim 18, wherein the plurality of photoelectric conversion units of the first detection sub-module has a same width as the plurality of photoelectric conversion units of the second detection sub-module in the second direction.

20. A medical device, comprising:

a housing defining a scanning chamber; and a detection assembly disposed in the housing, the detection assembly comprising a detector comprising a plurality of detector modules, each of the plurality of detector modules comprising a plurality of detection sub-modules at least partially arranged in a stepped manner in a first direction, wherein:

each of the plurality of detection sub-modules comprises a plurality of photoelectric conversion units arranged at intervals in a second direction intersecting with the first direction and one substrate, the plurality of photoelectric conversion units being disposed on the substrate to share the substrate;

one of two adjacent detection sub-modules is located at a higher step as a first detection sub-module, and the other one of the two adjacent detection sub-modules is located at a lower step and as a second detection sub-module;

a first gap is formed between the plurality of photoelectric conversion units of the first detection sub-module;

a second gap is formed between the plurality of photoelectric conversion units of the second detection sub-module;

a width of the first gap in the second direction is smaller than a width of the second gap in the second direction;

the plurality of detector modules is arranged in the second direction, and detection sub-modules of the plurality of detector modules at a same step are adjacent to each other; and the first direction is an extending direction of the scanning chamber.

* * * * *